United States Patent
Koyama et al.

(10) Patent No.: US 9,541,221 B2
(45) Date of Patent: Jan. 10, 2017

(54) TUBE CLAMP STRUCTURE OF TUBING PUMP

(71) Applicants: NAMIKI SEIMITSU HOUSEKI KABUSHIKI KAISHA, Tokyo (JP); Namiki Precision Singapore Pte. Ltd., Singapore (SG)

(72) Inventors: Masahiro Koyama, Tokyo (JP); Shouta Nakamura, Tokyo (JP); Makoto Kashiwagi, Tokyo (JP); Hiroyuki Kogure, Tokyo (JP); Hiroyuki Tajima, Tokyo (JP)

(73) Assignees: NAMIKI SEIMITSU HOUSEKI KABUSHIKI KAISHA, Tokyo (JP); NAMIKI PRECISION SINGAPORE PTE. LTD., Singapore (SG)

( * ) Notice: Subject to any disclaimer, the term of this patent is extended or adjusted under 35 U.S.C. 154(b) by 0 days.

(21) Appl. No.: 14/443,058

(22) PCT Filed: Nov. 14, 2013

(86) PCT No.: PCT/JP2013/080766
§ 371 (c)(1),
(2) Date: May 14, 2015

(87) PCT Pub. No.: WO2014/077309
PCT Pub. Date: May 22, 2014

(65) Prior Publication Data
US 2015/0285404 A1    Oct. 8, 2015

(30) Foreign Application Priority Data
Nov. 14, 2012 (JP) ................. 2012-250000

(51) Int. Cl.
*F16L 3/10* (2006.01)
*F04B 43/12* (2006.01)
*A61M 5/142* (2006.01)
*F16L 3/13* (2006.01)
*A61M 39/28* (2006.01)

(52) U.S. Cl.
CPC ............. *F16L 3/10* (2013.01); *A61M 5/14228* (2013.01); *A61M 39/28* (2013.01); *F04B 43/12* (2013.01); *F16L 3/13* (2013.01); *A61M 39/281* (2013.01)

(58) Field of Classification Search
CPC .... A61M 39/28; A61M 39/281; A61M 5/142; A61M 5/14228; A61M 5/00; F16L 3/10; F16L 3/13; F04B 43/12
(Continued)

(56) References Cited

U.S. PATENT DOCUMENTS 5,017,192 A * 5/1991 Dodge ................ A61M 39/287 251/7
5,401,256 A * 3/1995 Stone .................. A61M 39/287 251/10
(Continued)

FOREIGN PATENT DOCUMENTS

JP    3133453 U    7/2007
WO   2010/149232 A1   12/2010

OTHER PUBLICATIONS

International Search Report; PCT/JP2013/080766; Feb. 10, 2014.

*Primary Examiner* — Nkeisha Smith
(74) *Attorney, Agent, or Firm* — Studebaker & Brackett PC (57) ABSTRACT

PROBLEM: To reduce occurrence of an error of not closing a tube and to simplify a structure and an operation procedure.
SOLUTION: In a tube clamp structure of a tubing pump for closing a tube 30 attached to and detached from a pump body 10 by a clamp device 40, the clamp device 40 is equipped with: a first holding piece 41; a second holding piece 42 engaged to approach or separate from the first holding piece 41; and an urging member for urging these first holding piece 41 and second holding piece 42 in
(Continued)

approaching directions, is configured to hold and deform the tube 30 between these first holding piece 41 and second holding piece 42 for closing, and is detachably attached to the pump body 10.

4 Claims, 9 Drawing Sheets

(58) Field of Classification Search
USPC .......... 604/67, 246, 250, 151, 153; 248/74.2
See application file for complete search history.

(56) References Cited

U.S. PATENT DOCUMENTS

| | | | | |
|---|---|---|---|---|
| 5,567,120 | A * | 10/1996 | Hungerford | A61M 5/14212 417/474 |
| 6,117,115 | A * | 9/2000 | Hill | A61M 5/16813 604/250 |
| 6,261,262 | B1 * | 7/2001 | Briggs | A61M 5/142 251/7 |
| 2005/0033245 | A1 * | 2/2005 | Abrahamson | F04B 43/082 604/250 |
| 2007/0270765 | A1 * | 11/2007 | Hasler | A61M 5/14228 604/246 |
| 2010/0268161 | A1 * | 10/2010 | Traversaz | A61M 5/14244 604/151 |
| 2013/0211323 | A1 * | 8/2013 | Lee | A61M 5/14228 604/67 |
| 2014/0074047 | A1 * | 3/2014 | Calderon | A61M 39/28 604/250 |
| 2014/0336613 | A1 * | 11/2014 | Roth | A61M 39/284 604/500 |
| 2015/0018766 | A1 * | 1/2015 | Nakanishi | A61M 5/14228 604/151 |

* cited by examiner

TUBE CLAMP STRUCTURE OF TUBING PUMP

TECHNICAL FIELD

The invention relates to a tube clamp structure of a tubing pump for forcibly transferring a fluid in a tube in order to inject a medical fluid or the like to a patient.

BACKGROUND ART

Conventionally, for example, as described in Patent Document 1, this type of a tubing pump related to the invention is equipped with: a pump body (transfusion device 1); a door (11) openable or closable with respect to the pump body; a transfusion tube (2) attached between these pump body (transfusion device 1) and door (11); a slide clamp (21) attached to the transfusion tube (2) and opening and closing the tube; and a safety clamp (9) for automatically closing the transfusion tube (2) by opening of the door (11).

In this background art, the slide clamp (21) is attached to the transfusion tube (2), and the slide clamp (21) is slid. In this way, the transfusion tube (2) can be closed by a slit (23) of the slide clamp (21). Furthermore, the transfusion tube (2) can be attached to and detached from the transfusion device (1) while a closed state thereof by this slide clamp (21) is maintained. In addition, since the safety clamp (9) automatically closes the transfusion tube (2) by the opening of the door (11) during the attachment or detachment, it is possible to prevent a flow of the remaining fluid in the transfusion tube (2) that is caused by gravity.

However, according to the above background art, in the case where a worker forgets to perform a closing operation for sliding the slide clamp (21) as being distracted by another operation or the like, for example, after the slide clamp (21) is attached to the transfusion tube (2), the fluid in the transfusion tube (2) possibly flows by the gravity.

In addition, since two types of the clamps, which are the slide clamp (21) and the safety clamp (9), are used, structures, operation procedures, and the like thereof tend to be complicated.

CITATION LIST

Patent Literature

Patent Document 1: JP-A-5-277186

SUMMARY OF THE INVENTION

Problem to be Solved by the Invention

One example of a problem of the invention is to handle the above conventional situation. More specifically, purposes of the invention are to be able to reduce occurrence of an error of not closing a tube, to be able to simplify a structure and an operation procedure, and the like.

Solutions to the Problems

A solution to the above problem is a tube clamp structure of a tubing pump for closing a tube that is attached to and detached from a pump body by a clamp device, in which the clamp device is equipped with: a first holding piece; a second holding piece engaged with the first holding piece to approach or separate therefrom; and an urging member for urging these first holding piece and second holding piece in approaching directions, is configured to hold and deform the tube between these first holding piece and second holding piece for closing, and is detachably attached to the pump body.

Effects of the Invention

The invention is configured as above. Therefore, the purposes of the invention that are to be able to reduce the occurrence of the error of not closing the tube, to be able to simplify the structure and the operation procedure, and the like can be achieved.

DESCRIPTION OF EMBODIMENTS

A first characteristic of this embodiment is a tube clamp structure of a tubing pump having a clamp device that closes a tube attached and detached to and from a pump body, the clamp device including: a first holding piece; a second holding piece engaged with the first holding piece in a manner to approach and separate therefrom; and an urging member for urging the first and the second holding pieces in approaching directions, being configured to hold and deform the tube between the first and the second holding pieces for closing, and being detachably attached to the pump body.

According to this configuration, the tube is held in a space between the first holding piece and the second holding piece that is narrowed by an urging force of the urging member, and the tube is thereby deformed and closed. Thus, for example, even in the case where an operation with respect to the clamp device is not performed after the clamp device is attached to the tube, the tube can be maintained in a closed state by the urging force of the urging member.

As a second characteristic, the pump body is provided with an door that is openable and closable, the first holding piece and the second holding piece are configured such that, when both of operation parts thereof that are located on one side with a fulcrum being a boundary are closed, both of holding parts thereof that are located on the other side with the fulcrum being the boundary are opened, the urging member is provided to urge both of the holding parts in closing directions, and the operation part of the second holding piece is pushed to the first holding piece side by the door that is being closed in a state that the first holding piece is fixed to the pump body, so as to open a space between both of the holding parts.

According to this configuration, when the tube is clamped by the clamp device, both of the operation parts of the first holding piece and a holding movable body are closed to open both of the holding parts, the tube is arranged therebetween, and a force for closing both of the operation parts is reduced. In this way, both of the holding parts are closed by the urging force of the urging member, and hold and deform the tube for closing. Then, when the first holding piece is fixed to the pump body and the door is closed in this state, the operation part of the second holding piece is pushed by the door. Accordingly, the space between both of the holding parts is opened, and the tube is opened. Therefore, the tube can be opened by closing of the door without requiring a clamp device such as a conventional safety clamp other than the clamp device.

As a third characteristic, the fulcrum is set as a first fulcrum, a second fulcrum that can attach and detach the first holding piece to and from the pump body and supports the first holding piece to rotate with respect to the pump body for a specified amount is provided between the pump body and a portion on the holding part side of the first fulcrum in the first holding piece. After the first holding piece is attached to the pump body and rotates for the specified amount by the second fulcrum, the operation part of the second holding piece is pushed to the first holding piece side by the door that is being closed, and the second holding piece rotates with the first fulcrum being the fulcrum, so as to open the space between both of the holding parts.

According to this configuration, in the case where the tube that is closed by the clamp device is attached between the door and the pump body, the door is closed after the first holding piece is attached to the pump body and rotates for the specified amount. Then, the operation part of the second holding piece is pushed to the first holding piece side by this door. In this way, a holding guiding body rotates with the first fulcrum being the fulcrum, and both of the holding parts are opened. Therefore, the inside of the tube is opened from the closed state and is brought into a state that the fluid can flow therethrough by driving of a pump mechanism 50.

As a fourth characteristic, a locking part for locking the first holding piece that is attached to the pump body and has rotated for the specified amount, to the pump body in a manner capable of being locked or unlocked is provided.

According to this configuration, in the case where the first holding piece is attached to the pump body by the second fulcrum and this first holding piece then rotates for the specified amount, the first holding piece that has rotated for the specified amount is locked to the pump body in the manner capable of being locked or unlocked.

As a fifth characteristic, a handle for rotating the clamp device in a direction to separate from the pump body with the second fulcrum being the fulcrum is provided on the operation part side of the second support in the clamp device.

According to this configuration, when the clamp device is detached from the pump body, a finger is hooked on the handle, and a clamp body can rotate in the direction to separate from the pump with the second fulcrum being the fulcrum.

Next, a detailed description will be made on a preferred example that embodies the above embodiment on the basis of the drawings. It should be noted that the drawings from FIGS. 1 to 9 correspond to this example. In the following description, the number of the referred drawing is denoted in the parenthesis when the drawing that is particularly appropriate to be referred for a described portion is available.

EXAMPLE

Figure 1:
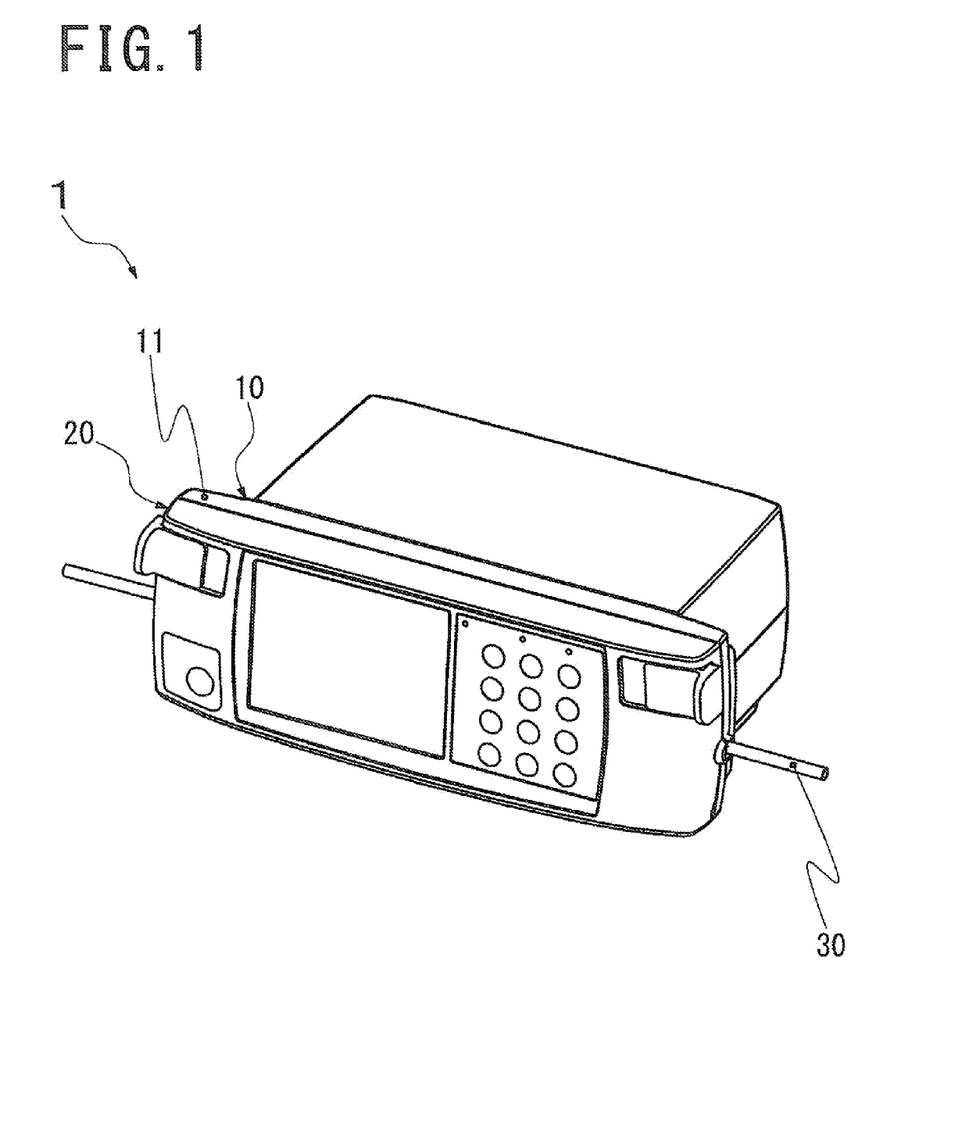
FIG. 1 is a perspective view of an example of a tubing pump to which a tube clamp structure according to the invention is applied.
Figure 2:
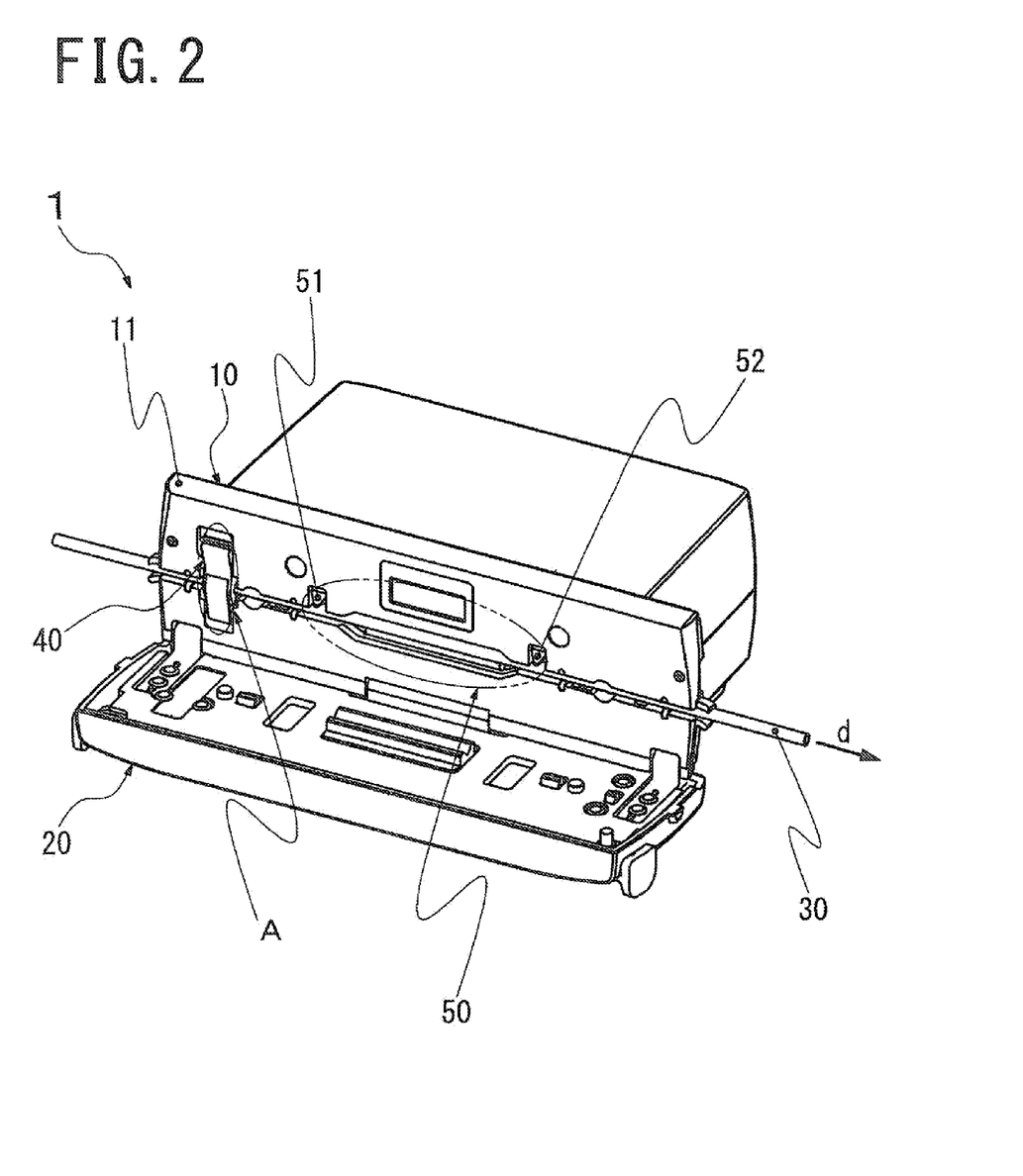
FIG. 2 is a perspective view of a state that a door is opened in the tubing pump.

FIGS. 1 and 2 depict a device that causes a fluid (for example, a medical fluid or a nutritional supplement) to forcibly flow in a tube by using a pump, so as to inject the fluid into a patient body, and depict external appearance of a tubing pump 1 to which a tube clamp structure A according to the invention is applied. This tubing pump 1 is equipped with a door 20 for opening and closing a front part of a pump body 10. FIG. 1 depicts a state that the door 20 is closed, and FIG. 2 depicts a state that the door 20 is opened.

The pump body 10 is formed in a substantially rectangular box shape and has a vertically arranged base 11 on a front side thereof that is opened or closed by the door 20. A tube 30 is transversely inserted through this base 11 (see FIGS. 1 to 5).

The base 11 is a substantially thick plate-shaped portion, and is equipped with a pump mechanism 50 for forcibly transferring the fluid in the attached tube 30. For example, as disclosed in JP-A-2007-23803 and Japanese Domestic Re-publication of PCT International Publication No. WO 2009/133705 A, the pump mechanism 50 forcibly transfers the fluid in the tube 30 in a d-direction that is indicated by an arrow in FIG. 2 by appropriately combining pressing/opening operations with respect to the attached tube 30, opening/closing operations of a valve 51 on an upstream side thereof, opening/closing operations of a valve 52 on a downstream side thereof, and the like (see FIG. 2).

Figure 3:
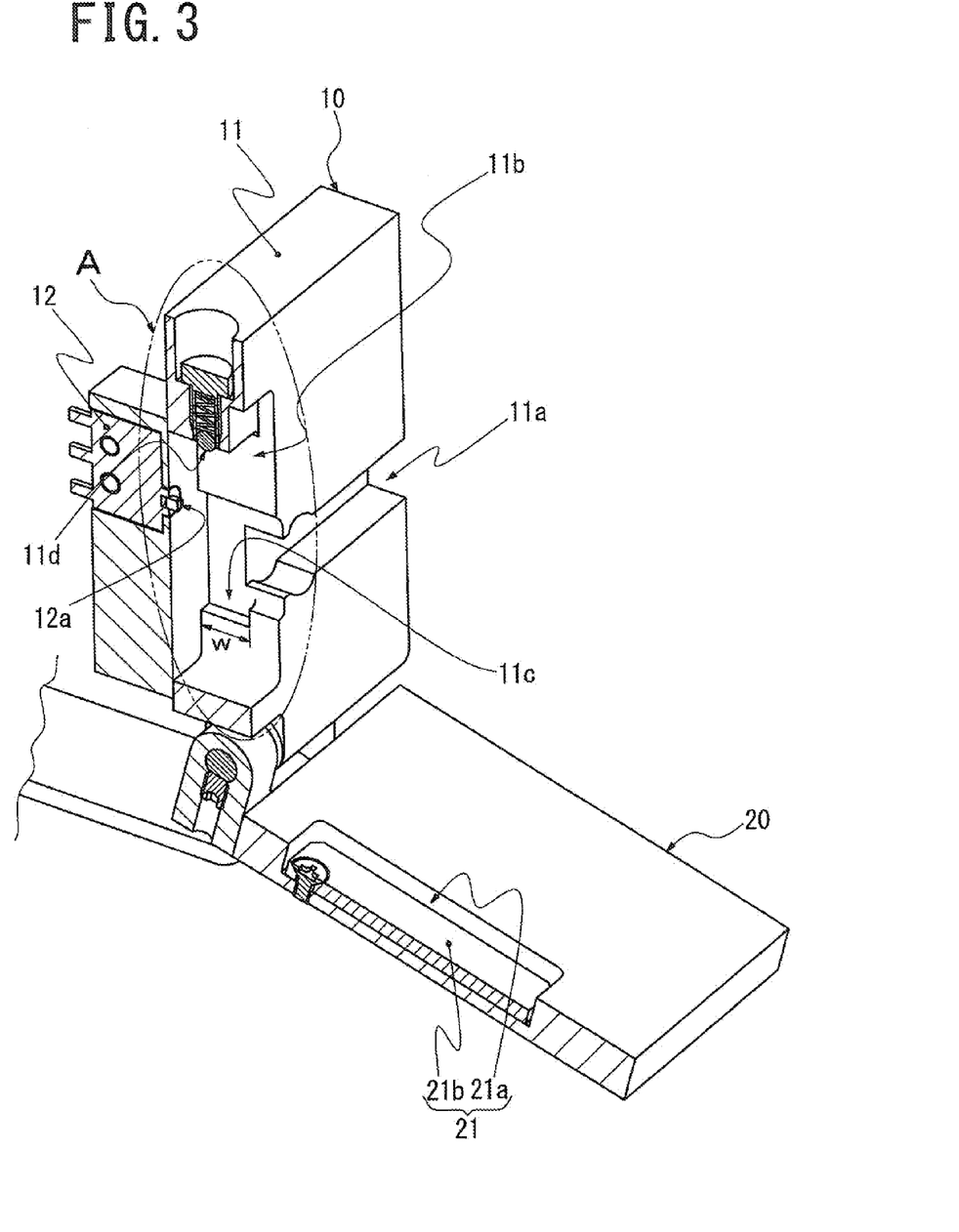
FIG. 3 is a cross-sectional perspective view of a main part that depicts an example of a pump body and the door.
Figure 4:
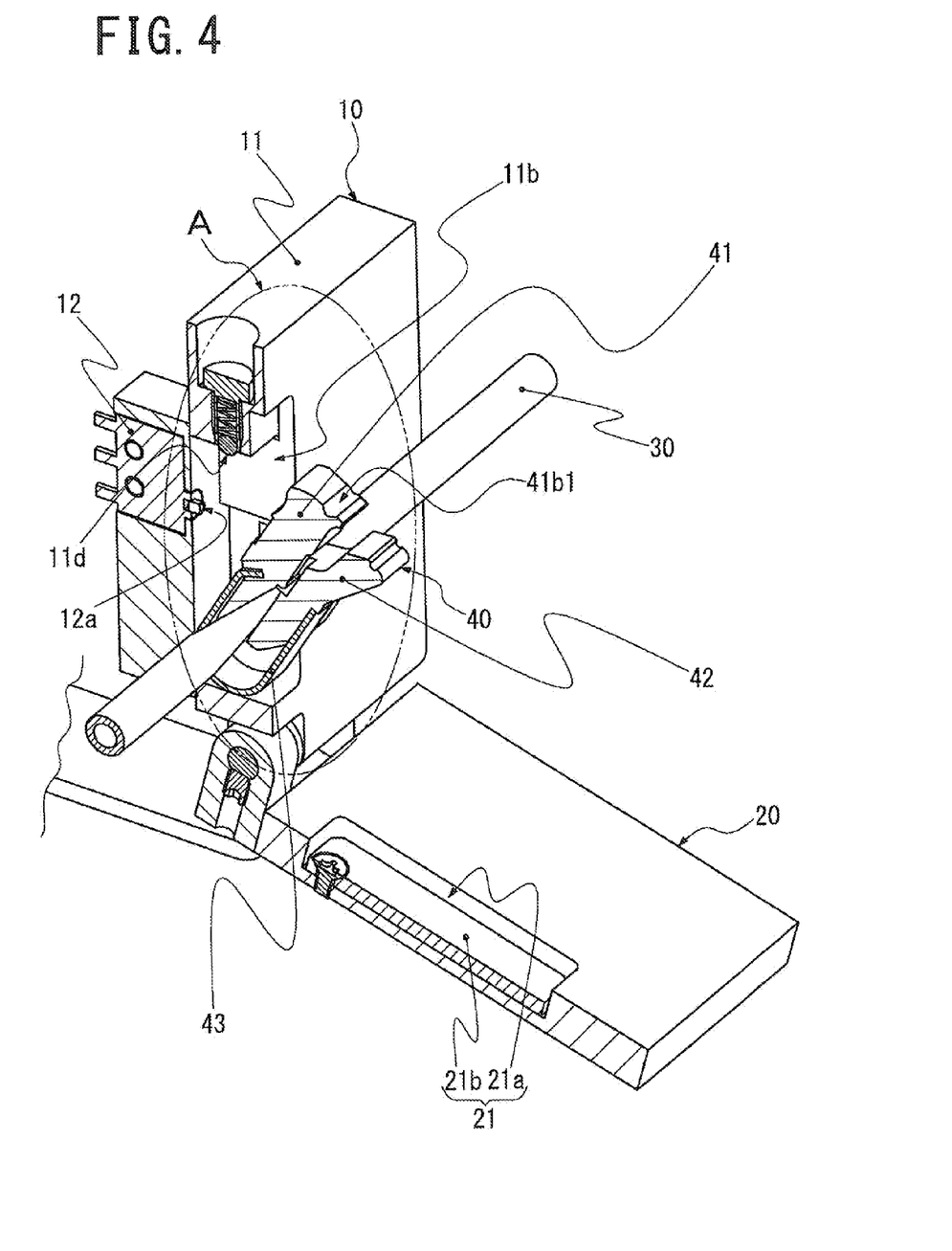
FIG. 4 is a cross-sectional perspective view of a main part that depicts a state that a tube and a clamp device are attached to the pump body.
Figure 5:
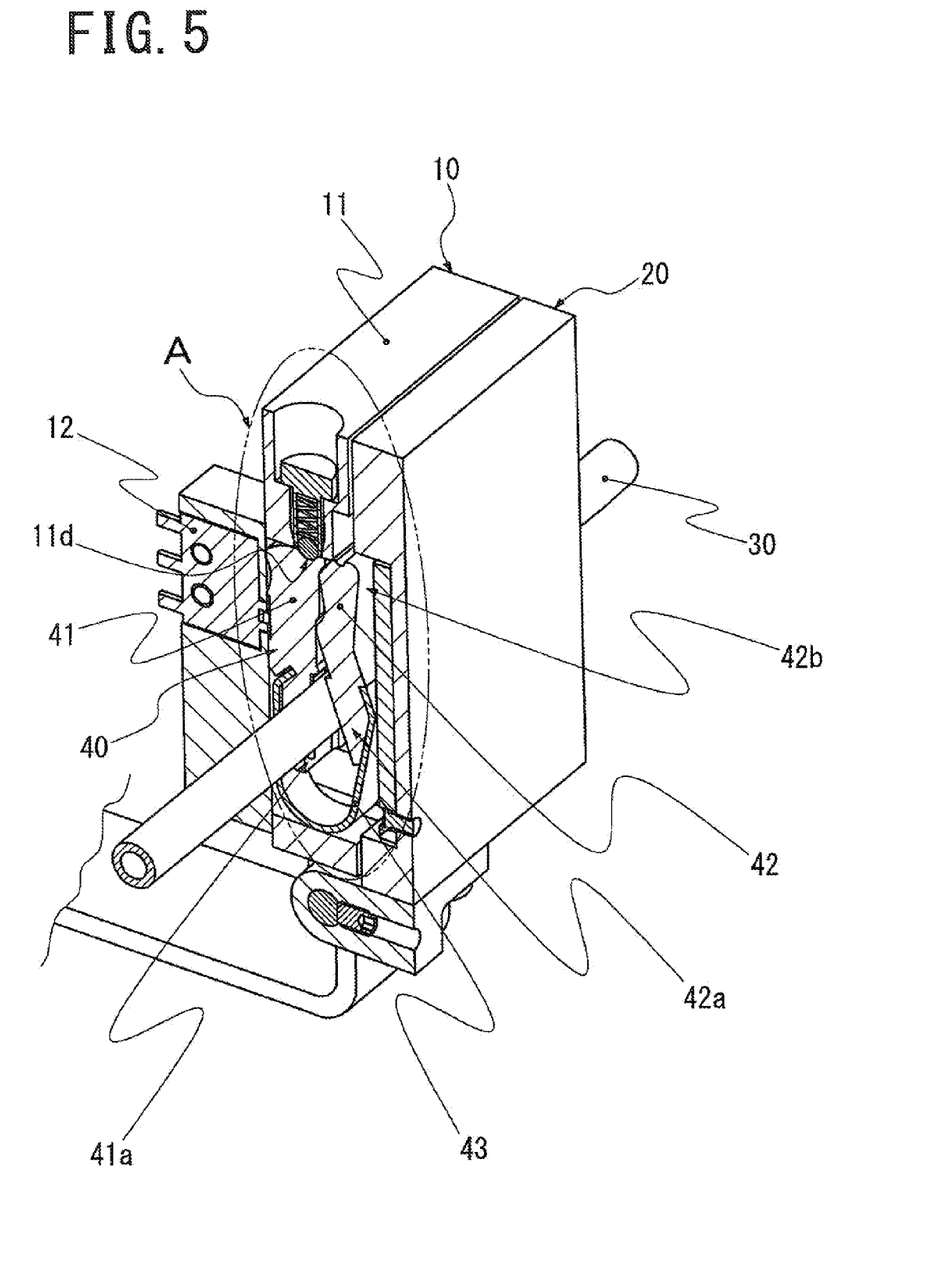
FIG. 5 is a cross-sectional perspective view of a main part that depicts a state that the door is closed.

This base 11 is provided with: a tube insertion groove 11a through which the tube 30 is fitted and inserted therethrough; a clamp fitting recess 11b to which a clamp device 40, which will be described below, is fitted; a clamp support 11c for supporting the clamp device 40 in a manner to allow attachment and detachment, and rotation thereof for a specified amount; a locking part 11d for locking the clamp device 40 that is attached thereto and has rotated for the specified amount in a manner to allow locking and unlocking thereof, and the like (see FIGS. 3 and 4).

In addition, on a back side of the base 11, a clamp detection sensor 12 for detecting the clamp device 40 that has rotated until being locked by the locking part 11d is provided.

The tube insertion groove 11a is a recessed groove that is formed in a perpendicular surface of the base 11 in a manner to continue in a substantially horizontal direction, the base 11 being opened or closed by the door 20. The tube 30 is attached to and detached from a front side thereof (a right direction side in FIG. 6).

The clamp fitting recess 11b is formed in a substantially recessed shape in a perpendicular surface of the base 11 in a manner to communicate with the tube insertion groove 11a, and secures a space for including the clamp device 40 that holds the tube 30.

The clamp support 11c is a recess that is provided in the clamp fitting recess 11b to support a supported projection 41a2 on a tip side of the clamp device 40 in a manner to allow attachment and detachment, and rotation thereof for a specified amount.

As it will be described in detail, this clamp support 11c is provided in both of a wall surface on a deep side in an insertion direction of the tube 30 (a surface on a deep side depicted in FIG. 3) and a wall surface on a near side (a surface on a near side not depicted in FIG. 3) of an inner wall of the clamp fitting recess 11b of the base 11. Then, the clamp support 11c on the deep side is formed in a recessed shape that is opened upward and in a near direction (a near direction in FIG. 3) and closed at both ends in a thickness direction of the base 11 such that the supported projection 41a2 of the clamp device 40 is inserted therein from above. The clamp support on the near side (not depicted) is also formed in a symmetrical manner thereto.

A width w (see FIG. 3) of the each clamp support 11c in the thickness direction of the base 11 is set to be larger than a width of the supported projection 41a2 of the clamp device 40 (in detail, a diameter of the supported projection 41a2 in a substantially columnar shape) such that the clamp device 40 slightly moves in the thickness direction of the base 11.

According to this configuration, during attachment work in which the supported projection 41a2 at a tip of the clamp device 40 is fitted to the clamp support 11c (see FIG. 6) and the clamp device 40 is rotated to a normal position (a position depicted in FIG. 7), allowance in the thickness direction of the base 11 is secured. Thus, for example, compared to a case where the clamp support 11c is supposedly formed to have a cylindrical surface that follows the supported projection 41a2 at the tip of the clamp device 40, the attachment work can easily and smoothly be performed.

It should be noted that, in the depicted example, the clamp support 11c on the pump body 10 side is the recess, the supported projection 41a2 on the clamp device 40 side is the projection, and these are fitted to each other. However, as another example, a recessed and projected relationship therebetween can be reversed.

The locking part 11d is a so-called ball plunger that is configured by including: a ball that is projected downward toward the inside of the clamp fitting recess 11b and is rotatably supported; a spring that urges the ball to be retractable; and a retaining part that retains these ball and spring. In this locking part 11d, the ball that is directed downward is fitted to the clamp device 40 that has rotated for the specified amount in a manner capable of being fitted or unfitted.

The clamp detection sensor 12 is a micro switch that outputs a contact signal when being pressed by the clamp device 40 that has rotated for the specified amount. According to the depicted example, an actuator 12a of a push-button type is arranged to be directed to the inside of the clamp fitting recess 11b and face a first holding piece 41 (see FIGS. 4 and 5).

This clamp detection sensor 12 can be replaced with a contact sensor in another mode, a noncontact sensor such as an infrared switch, or the like.

The door 20 is a substantially plate-shaped member that is pivotally supported to be rotatable on a lower end side of the base 11, and closes by covering or opens the perpendicular surfaces on the tube insertion groove 11a side and the clamp fitting recess 11b side of the base 11. When this door 20 is closed and superimposed on the base 11, so as to be completely closed, a closed state thereof is retained by a catch mechanism, urging unit, or the like (not depicted) that is provided between the base 11 and the door 20 or in a hinge portion.

A pressing part 21 for pressing the clamp device 40 that is attached to the base 11 is provided on an inner surface side of this door 20. This pressing part 21 is configured by including: a recess 21a that is fitted to an operation part 42b of the clamp device 40 in a manner capable of being fitted or unfitted; and a pressing piece 21b that is provided in the recess 21a. The pressing piece 21b is detachably fixed to an inner surface of the recess 21a by a fixing tool (for example, a screw and a bolt) such that it can be exchanged when wear, settling, or the like thereof is generated due to abutment against the clamp device 40.

In addition, the tube 30 is a circular tube that is made of a transparent synthetic resin, is squished and closed by a pressing force in a radial direction, and elastically restores an original shape when the pressing force is canceled.

Figure 8:
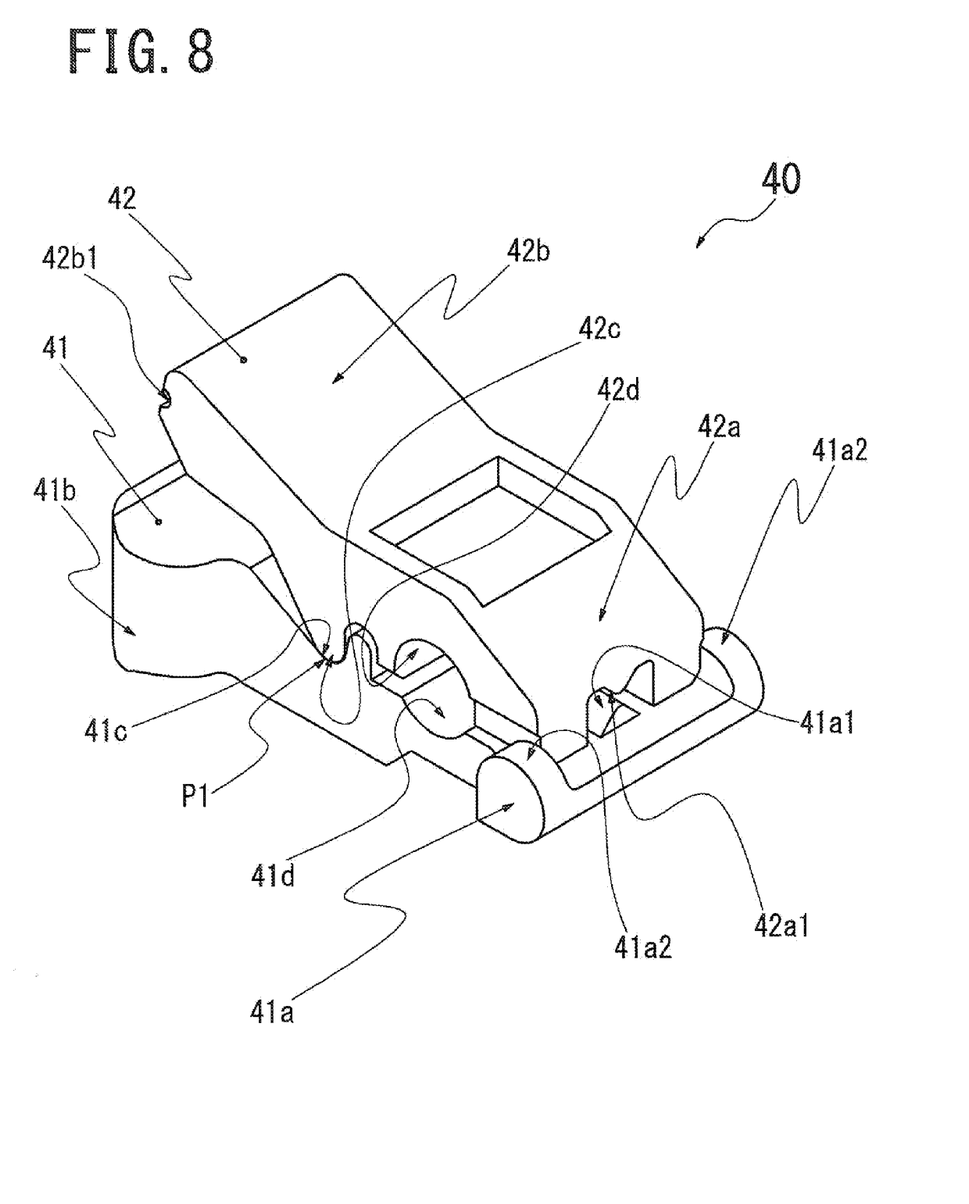
FIG. 8 is a perspective view of an example of the clamp device.

FIG. 8 depicts a state that an urging member 43 is detached from the clamp device 40. As particularly depicted in this FIG. 8, the clamp device 40 is equipped with: the first holding piece 41; a second holding piece 42 that is engaged to bring a holding part 42a closer to or away from the first holding piece 41; the urging member 43 (not depicted in FIG. 8) that urges these first holding piece 41 and second holding piece 42 in approaching directions, is configured by closing both of the operation parts 41b, 42b that are located on one side (an upper side in FIG. 6) with a first fulcrum P1 being a boundary to open both of the holding parts 41a, 42a that are located on another side (a lower side in FIG. 6) with the first fulcrum P1 being the boundary, and holds and deforms the tube 30 between the holding part 41a of the first holding piece 41 and the holding part 42a of the second holding piece 42 for closing.

Figure 6:
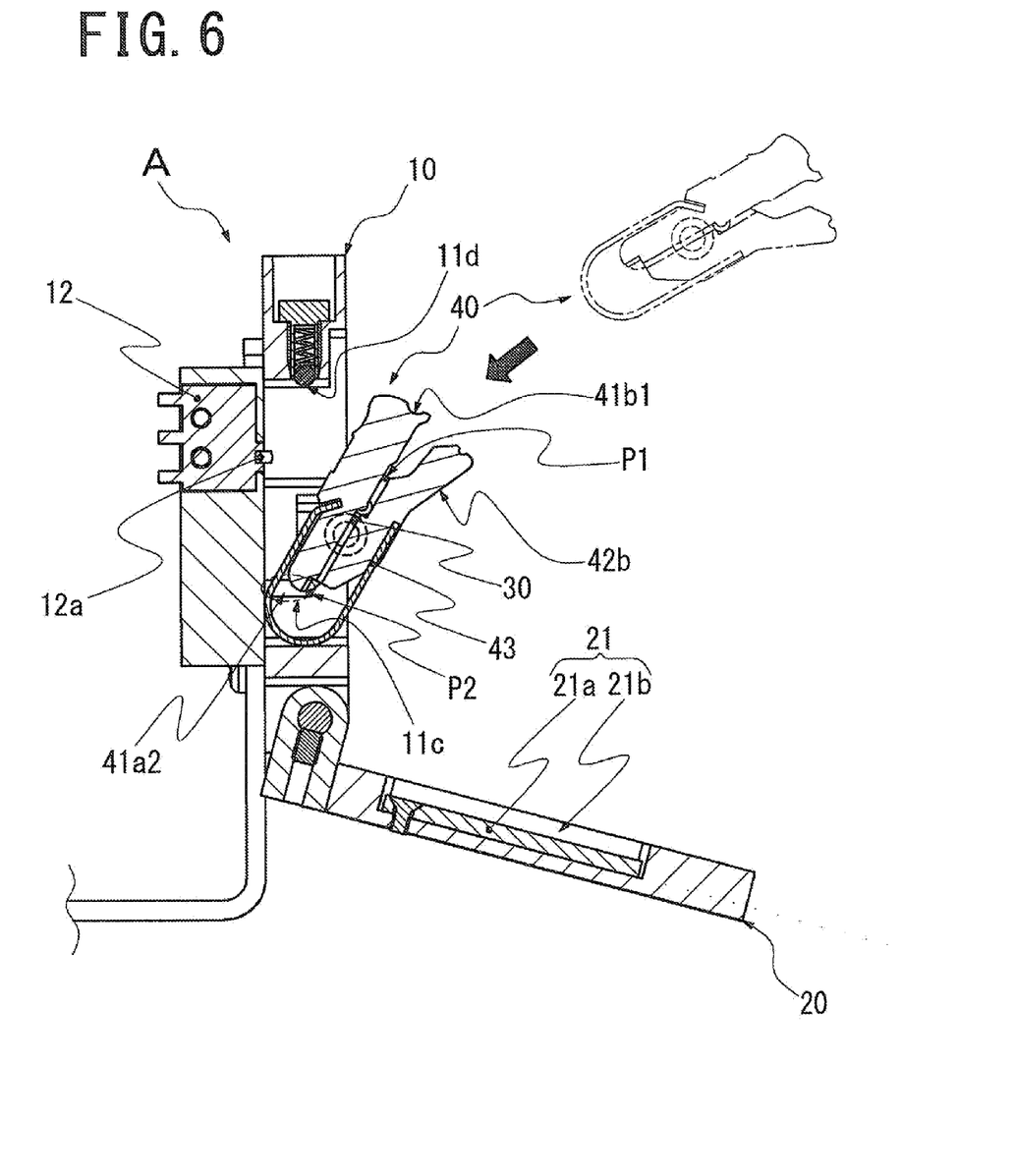
FIG. 6 is a cross-sectional view of a main part that depicts a state that the tube and the clamp device are attached to the pump body.
Figure 9:
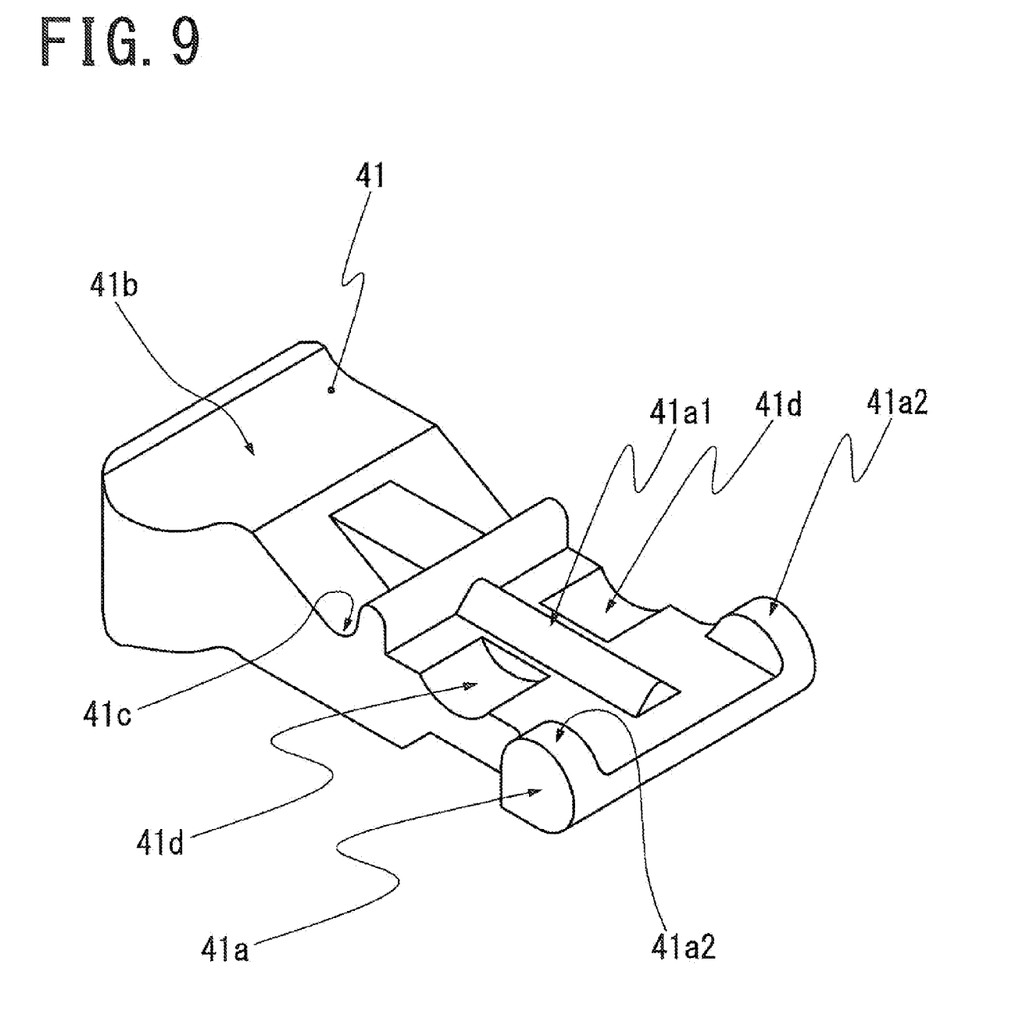
FIG. 9 is a perspective view of an example of a first holding piece in the clamp device.

The first holding piece 41 has the holding part 41a on a tip side, has the operation part 41b on a rear end side, and has a support recess 41c that constitutes the first fulcrum P1 between these holding part 41a and operation part 41b (see FIGS. 6, 8, and 9).

The holding part 41a is a portion that is located on a front side of the first fulcrum P1 in the first holding piece 41, and has a holding projection 41a1 that is projected to the second holding piece 42 side near a center in a width direction of a surface that faces the second holding piece 42. This holding projection 41a1 is a projection that has a substantially mountain-shaped cross part and linearly continues in a front-rear direction of the first holding piece 41 (see FIG. 9). This holding projection 41a1 approaches or separates from a holding projection 42a1 of the second holding piece 42, and holds the tube 30 between the holding projection 41a1 and the holding projection 42a1 when approaching.

On both sides in a width direction of the first holding piece 41 with this holding part 41a being placed therebetween, a tube retainer 41d that has a substantially semi-cylindrical surface is provided to be substantially orthogonal to the holding projection 41a1. This tube retainer 41d cooperates with a tube retainer 42d of the opposing second holding piece 42, so as not to press the tube 30 cooperatively.

In addition, the supported projection 41a2 that is fitted to the clamp support 11c of the base 11 is provided at an extreme tip of this holding part 41a. This supported projection 41a2 is a substantially columnar projection that can be fitted to or unfitted from the clamp support 11c (see FIG. 9), and constitutes a second fulcrum P2 for rotating the second holding piece 42 for the specified amount when being fitted to the clamp support 11c (see FIG. 6). Furthermore, as one example depicted in FIGS. 8 and 9 will be described further in detail, two of the supported projection 41a2 are provided on both sides in the width direction at the extreme tip of the first holding piece 41, and each thereof is fitted to the clamp support 11c of the base 11.

The operation part 41b is a portion that is located on a rear side of the first fulcrum P1 in the first holding piece 41. In this operation part 41b, an extreme rear end surface of the first holding piece 41 is formed with a locked recess 41b1 in a substantially hemispherical shape, to which the ball of the locking part 11d is fitted (see FIGS. 6 to 8).

Furthermore, the support recess 41c is formed in a substantially recessed curve shape that is fitted to a support projection 42c of the second holding piece 42, which will be described below, and constitutes the first fulcrum P1 (see FIGS. 8 and 9).

The second holding piece 42 has the holding part 42a on a tip side, has the operation part 42b on a rear end side, and has the support projection 42c that constitutes the first fulcrum P1 between these holding part 42a and operation part 42b (see FIG. 8).

The holding part 42a is a portion that is located on a front side of the first fulcrum P1 in the second holding piece 42, and has the holding projection 42a1 that is projected to the first holding piece 41 side near a center in a width direction of a surface that faces the first holding piece 41. This holding projection 42a1 is a projection that has a substantially mountain-shaped cross part and linearly continues in a front-rear direction of the second holding piece 42 (see FIG. 8), and holds the tube 30 between the holding projection 42a1 and the holding projection 41a1 of the first holding piece 41.

On both sides in a width direction of the second holding piece 42 with this holding part 42a being placed therebetween, the tube retainer 42d that has a substantially semi-cylindrical surface is provided to be substantially orthogonal to the holding projection 42a1. Together with the tube retainer 41d of the opposing first holding piece 41, this tube retainer 42d retains the tube 30 so as not to press the tube 30.

According to these tube retainers 41d, 42d and holding projections 41a1, 42a1, when the tube 30 is held by both of the holding parts 41a, 42a, the tube 30 is retained in a substantially linear shape by the tube retainers 41d, 42d. A center in a longitudinal direction of the tube 30 can be held and deformed to be squished by both of the holding projections 41a1, 41a2 in a substantially orthogonal direction. Furthermore, a favorable closed state in which leakage or the like is less likely to occur can be obtained.

The operation part 42b is a portion that is located on the rear side of the first fulcrum P1 in the second holding piece 42. This operation part 42b is formed to be projected to the door 20 side from the surface of the base 11 in a state that the clamp device 40 is locked in the locking part 11d of the base 11 (see FIG. 7).

An extreme rear end surface of this operation part 42b is formed with a handle 42b1 in a substantially recessed shape for causing the clamp device 40 to rotate in a direction to separate from the pump body 10 (the right direction in FIG. 7) with the second fulcrum P2 being a fulcrum.

The support projection 42c is a substantially semi-columnar projection that is fitted to the support recess 41c of the first holding piece 41 and constitutes the first fulcrum P1, and causes the second holding piece 42 to swing with a center line thereof being a reference (see FIG. 8).

Moreover, the urging member 43 is a substantially U-shaped plate spring, is provided to cover across the tip sides of the first holding piece 41 and the second holding piece 42, is locked at one end on the tip side of the first fulcrum P1 in the first holding piece 41, is locked at another end on the tip side of the first fulcrum P1 in the second holding piece 42, and urges both of the holding parts 41a, 42a of these first holding piece 41 and second holding piece 42 in closing directions (see FIGS. 4 to 7).

In the clamp device 40 with the above configuration, the tube 30 is held between both of the holding parts 41a, 42a. According to this example, this holding work is performed during assembling work of the clamp device 40. However, as another example, the tube 30 may be inserted between both of the holding parts 41a, 42a after the clamp device 40 is completed.

Next, characteristic operational effects of the tubing pump 1 with the above configuration will be described in detail.

First, in a state that the pump body 10 is separated from the tube 30 and the clamp device 40, the tube 30 is partially squished and closed when being held by both of the holding parts 41a, 42a of the clamp device 40. This closed state is maintained by an urging force of the urging member 43 of the clamp device 40 (see the clamp device 40 that is indicated by a two-dot chain line in FIG. 6).

Accordingly, in the state, even in the case where a worker does not perform any operation with respect to the clamp device 40 as being distracted by another operation or the like, for example, a closed portion of the tube 30 is not opened, and it is further possible to prevent a flow of the fluid in the tube 30.

Next, the tube 30 and the clamp device 40 are attached to the pump body 10 while the closed state is maintained. At this time, the door 20 is opened from the pump body 10, and the supported projection 41a2 at the tip of the first holding piece 41 is fitted to the clamp support 11c of the base 11 (see FIGS. 4 and 6).

Figure 7:
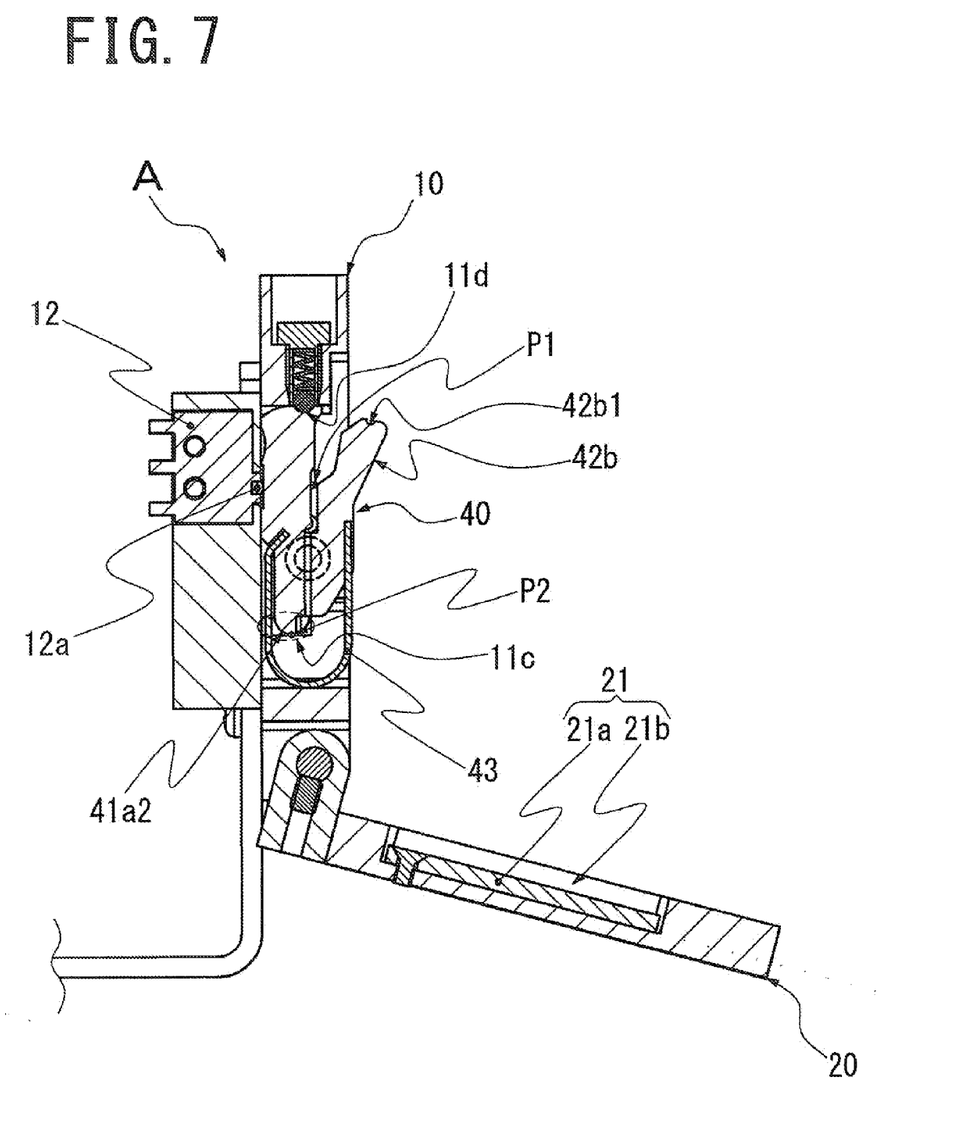
FIG. 7 is a cross-sectional view of a main part that depicts a state that the clamp device attached to the pump body rotates to a specified position.

Then, when the rear end side of the second holding piece 42 is pushed to the base 11 side by hand, the clamp device 40 rotates to the base 11 side with the second fulcrum P2 being the fulcrum, the locked recess 41b1 at the rear end of the first holding piece 41 is fitted to the locking part 11d, and the first holding piece 41 pushes the actuator 12a of the clamp detection sensor 12 almost simultaneously (see FIG. 7).

Accordingly, the clamp device 40 is unrotatably locked in the clamp fitting recess 11b of the base 11, and the contact signal indicative of a state that the clamp device 40 is locked in the locking part 11d is output from the clamp detection sensor 12.

In addition, the tube 30 that is held and closed by the second holding piece 42 is fitted to the tube insertion groove 11a of the base 11 and retained while extending in the substantially horizontal direction.

Next, when the door 20 is closed, the operation part 42b of the second holding piece 42 in the clamp device 40 is pushed by the closing door 20. Accordingly, a space between both of the holding parts 41a, 42a on the tip sides of the first holding piece 41 and the second holding piece 42 is opened, and the tube 30 that is held therebetween restores the original circular shape and cancels the closed state (see FIG. 5). Thus, the inside of the tube 30 is brought into a state that the fluid can flow, and the medical fluid or the like is forcibly transferred by the actuation of the pump mechanism 50.

It should be noted that, in the case where the clamp device 40 is unlocked from the locking part 11d due to some abnormality, an erroneous operation, or the like, this abnormal state can be recognized by the contact signal that is output from the clamp detection sensor 12.

In addition, when the tube 30 and the clamp device 40 are detached from the pump body 10, the actuation of the pump mechanism 50 is stopped, and the door 20 is opened. In this way, the operation part 42b of the clamp device 40 is no longer pushed by the door 20. Accordingly, both of the holding parts 41a, 42a of the clamp device 40 are closed by the urging force of the urging member 43, and the tube 30 is brought into the closed state by being held therebetween (see FIG. 7). Therefore, it is possible to prevent the fluid in the tube 30 from flowing by own weight.

Then, a finger is hooked on the handle 42b1 and pulls the handle 42b1 to the near side while the closed state is maintained. In this way, the clamp device 40 rotates in the near direction with the second fulcrum P2 being the fulcrum, and is brought into a state of being detachable from the pump body 10 (see FIGS. 4 and 6). Since the operation part 41b separates from the actuator 12a of the clamp detection sensor 12 almost simultaneously, the contact signal indicative of this state is output from the clamp detection sensor 12.

Then, during or after detachment work of the tube 30 and the clamp device 40 from the pump body 10, the closed state of the tube 30 is retained by the urging force of the urging member 43 even without need of the operation by the worker.

It should be noted that the clamp device 40 is configured such that the second holding piece 42 rotates with respect to the first holding piece 41 in the above example. However, as other examples of this clamp device, an aspect that a guide member is provided between a first holding piece and a holding guiding body and the second holding piece slides along the guide member, so as to approach or separate from the first holding piece, and an aspect that a metallic plate material or wire material that can elastically be deformed is subjected to bending so as to be formed in an integral shape having the same holding parts and operation parts can be raised.

In addition, in the above example, as a preferred example of the structure that allows the attachment and detachment of the clamp device 40, the supported projection 41a2 on the tip side of the clamp device 40 is fitted to the recessed clamp support 11c on the pump body 10 side. However, as another example of this attachment and detachment structure, an aspect that the pump body 10 is provided with a detachable shaft member and this shaft member is inserted through an appropriate position of the clamp device 40 can be raised.

In addition, according to the above example, the urging member 43 is the substantially U-shaped plate spring. However, this urging member 43 only needs to urge both of the holding parts 41a, 42a in the closing direction. As other examples thereof, a tension spring for urging a portion on the front side of the first fulcrum P1 in the clamp device 40 in the closing direction, and a compression spring for urging a portion on the rear side of the first fulcrum P1 in the clamp device 40 in an opening direction can be raised. Furthermore, as the other example of the urging member 43, an aspect that utilizes an elastic body other than the plate spring, such as a coil spring or rubber, can be raised.

In addition, the above locking part 11d only needs to have a mechanism that locks the rear end of the clamp device 40 when the clamp device 40 is fitted to the clamp support 11c and rotates for the specified amount and that cancels the locked state when the clamp device 40 is pulled in an opposite direction. As another example of this locking part 11d, an aspect that a locking piece or the like is locked to the clamp device 40 that has rotated for the specified amount in a manner capable of being locked or unlocked, the locking piece being formed of a roller that is supported to be elastically retracted or a plate spring, can be raised.

In addition, according to the above example, the handle 42b1 is the recess that is provided at the rear end of the second holding piece 42. However, this handle 42b1 only needs to be located on the rear end side of the second fulcrum P2 in the clamp device 40 and be easily operated by hooking the finger. As other examples of this handle 42b1, a projection that is projected from the second holding piece 42 to the door 20 side and an annular member can be raised.

In addition, according to the above example, in particular, in order to facilitate parallel arrangement of the plural tubing pumps 1 in a vertical direction, the tube clamp structure A is adopted for the tubing pump 1, through which the tube 30 is inserted in the horizontal direction. However, as another example, a tube clamp structure that is substantially the same structure as the above tube clamp structure A can be applied to a tubing pump through which the tube 30 is inserted in a perpendicular direction or a diagonal direction.

LIST OF THE REFERENCE NUMERALS

1 Tubing pump
10 Pump body
11 Base
11d Locking part
20 Door
30 Tube
40 Clamp device
41 First holding piece
41a Holding part
41b Operation part
42 Second holding piece
42a Holding part
42b Operation part
42b1 Handle
43 Urging member
A Tube clamp structure
P1 First fulcrum
P2 Second fulcrum

The invention claimed is:

1. A tube clamp structure of a tubing pump, comprising a clamp device that closes a tube attached and detached to and from a pump body, the clamp device including: a first holding piece; a second holding piece engaged with the first holding piece in a manner to approach and separate therefrom; and an urging member for urging the first and the second holding pieces in approaching directions, being configured to hold and deform the tube between the first and the second holding pieces for closing, and being detachably attached to the pump body, wherein the pump body is provided with an door that is openable and closable, the first holding piece and the second holding piece are configured that, when both of an operation part of the first holding piece and an operation part of the second holding piece located on one side with a first fulcrum being a boundary are closed, both of a holding part of the first holding piece and a holding part of the second holding piece located on another side with the first fulcrum being the boundary are opened, the urging member is provided to urge both of the holding parts of the first and second holding pieces in closing directions, and the operation part of the second holding piece is pushed to a first holding piece side by the door that is being closed, so as to open a space between both of the holding parts of the first and second holding pieces in a state that the first holding piece is fixed to the pump body, a second fulcrum that can attach and detach the first holding piece to and from the pump body and supports the first holding piece to rotate with respect to the pump body for a specified amount is provided between the pump body and a portion on a holding part side of the first fulcrum in the first holding piece, after the first holding piece is attached to the pump body and rotates for the specified amount by the second fulcrum, the operation part of the second holding piece is pushed to the first holding piece side by the door that is being closed, the second holding piece rotates with the first fulcrum, and the space between both of the holding parts of the first and second holding pieces is opened.

2. The tube clamp structure of the tubing pump according to claim 1, wherein a locking part for locking the first holding piece that is attached to the pump body and has rotated for the specified amount, to the pump body in a manner capable of being locked or unlocked is provided.

3. The tube clamp structure of the tubing pump according to claim 2, wherein a handle, for rotating the clamp device in a direction to separate from the pump body with the second fulcrum, is provided on the operation part of the second holding piece in the clamp device.

4. The tube clamp structure of the tubing pump according to claim 1, wherein a handle, for rotating the clamp device in a direction to separate from the pump body with the second fulcrum, is provided on the operation part of the second holding piece in the clamp device.

* * * * *